(12) United States Patent
Tanaka

(10) Patent No.: US 7,922,386 B2
(45) Date of Patent: Apr. 12, 2011

(54) THERMAL ANALYSIS APPARATUS

(75) Inventor: Nobuhiro Tanaka, Koganei (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 865 days.

(21) Appl. No.: 11/861,332

(22) Filed: Sep. 26, 2007

(65) Prior Publication Data

US 2008/0181281 A1    Jul. 31, 2008

(30) Foreign Application Priority Data

Sep. 27, 2006 (JP) ................................. 2006-262561

(51) Int. Cl.
*G01N 25/00* (2006.01)
(52) U.S. Cl. ............... 374/14; 374/12; 374/31; 374/208
(58) Field of Classification Search .................. 374/10, 374/12, 14, 31, 100, 43, 44, 45, 208; 177/157, 177/159, 212, 206
See application file for complete search history.

(56) References Cited

U.S. PATENT DOCUMENTS

| 3,074,270 | A | * | 1/1963 | Rabb .................................. 73/76 |
| 3,271,996 | A | * | 9/1966 | Ferenc et al. ................... 374/10 |
| 3,373,598 | A | * | 3/1968 | Johnson et al. ................. 374/14 |
| 4,596,470 | A | * | 6/1986 | Park ................................ 374/14 |
| 5,293,404 | A | | 3/1994 | Takeda |
| 6,057,516 | A | * | 5/2000 | Nakamura et al. ............ 177/212 |
| 6,257,757 | B1 | * | 7/2001 | Nakamura ..................... 374/14 |
| 6,860,136 | B1 | * | 3/2005 | Hay et al. ....................... 73/1.01 |
| 7,444,880 | B2 | * | 11/2008 | Zhang et al. ..................... 73/779 |
| 2003/0007542 | A1 | * | 1/2003 | Peterman et al. ............... 374/14 |
| 2007/0009009 | A1 | * | 1/2007 | Dziki ............................ 374/101 |
| 2008/0144694 | A1 | * | 6/2008 | Danley et al. ................... 374/14 |

FOREIGN PATENT DOCUMENTS

| FR | 2 360 064 | 2/1978 |
| FR | 2 543 683 | 10/1984 |
| JP | 4-361145 (A) | 12/1992 |
| JP | 2005-331432 (A) | 12/2005 |
| WO | WO 2006/090247 | 8/2006 |

OTHER PUBLICATIONS

European Search Report in Application No. 07253757.4-2204 dated Dec. 27, 2007.

* cited by examiner

*Primary Examiner* — Gail Verbitsky
(74) *Attorney, Agent, or Firm* — Buchanan Ingersoll & Rooney PC

(57) ABSTRACT

A thermal analysis apparatus includes: a sample temperature control device for surrounding a sample placed on a measurement position and controlling the temperature of the sample; a balance beam for supporting the sample and capable of tilting about a pivot point; and a sample moving device that allows the balance beam to slide between a first position at which the sample is situated at the measurement position and a second position at which the sample is situated at a distant position which is a position outside the sample temperature control unit. The distant position is a position which is deviated laterally from a line trajectory extending from the measurement position to the outside of the sample temperature control device. When the sample is at the measurement position, the balance beam is allowed to linearly slide and subsequently to rotationally slide about an axial line, to thereby transport the sample from the measurement position to the distant position.

15 Claims, 11 Drawing Sheets

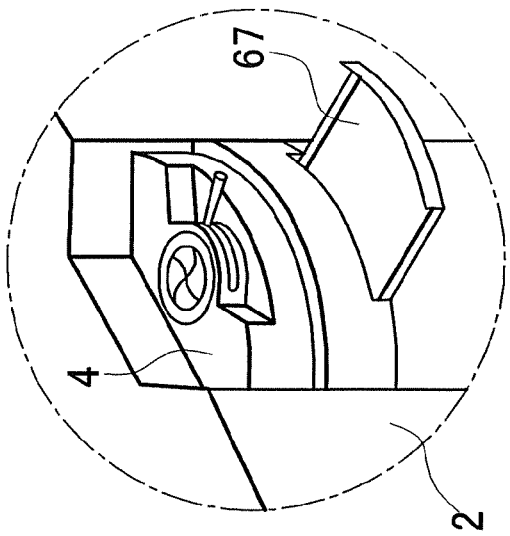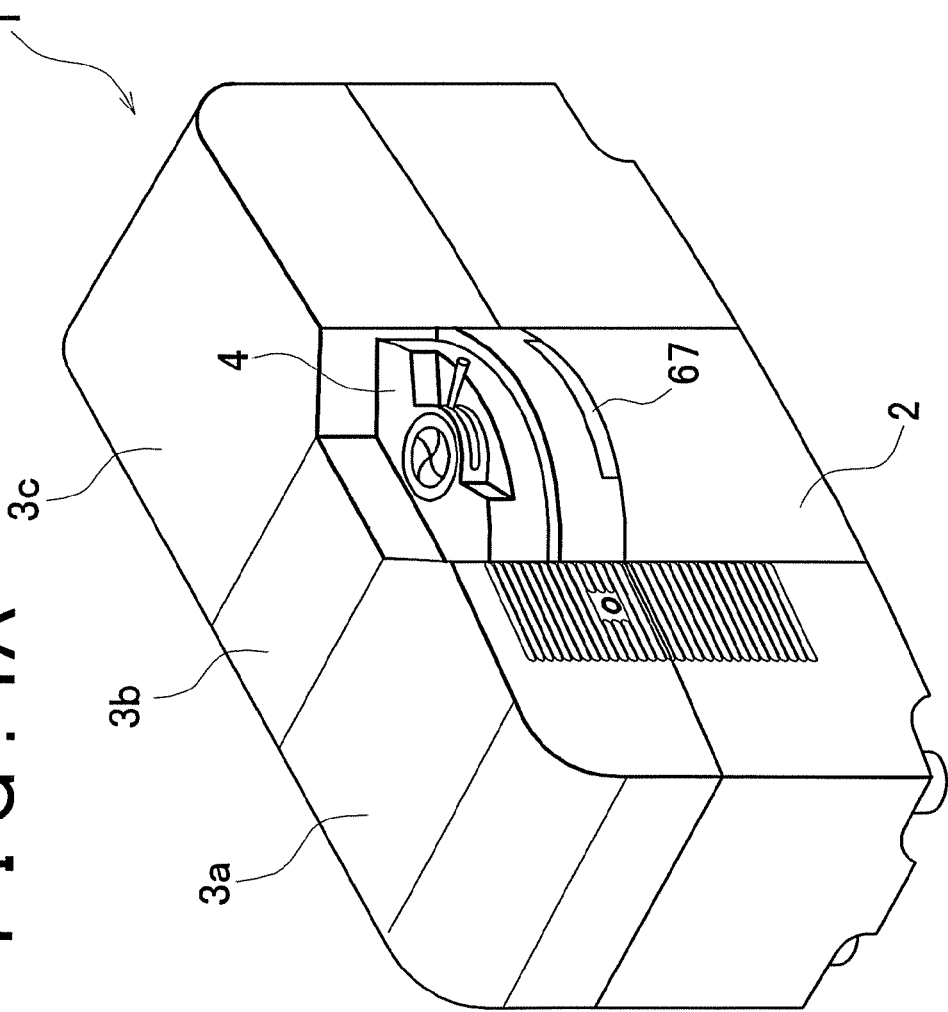

THERMAL ANALYSIS APPARATUS

BACKGROUND OF THE INVENTION

1. Field of the Invention

The present invention relates to a thermal analysis apparatus for measuring thermal characteristics of a sample while controlling the temperature of the sample.

2. Description of the Related Art

There have been known various types of thermal analysis apparatuses, such as a TG (Thermogravimetory) apparatus, a DTA (Differential Thermal Analysis) apparatus, and a DSC (Differential Scanning Calorimetory) apparatus. The TG apparatus measures a weight change of a sample with respect to a temperature change or a time lapse. The DTA apparatus simultaneously heats a reference substance being stable in a thermal characteristics and a sample of interest, and then measures a temperature difference exhibited between the reference substance and the sample at the time when the sample reacts to a heat. Thus, the DTA apparatus can detect, based on the temperature difference occurred, a thermal change having been occurred in the sample. The DSC apparatus measures the amount of heat when endothermic reaction or exothermic reaction occurs in the sample while it is heated, cooled, or held at a constant temperature. In addition, there have been known apparatuses that analyze a gas generated from a substance while it is heated. Known as such apparatuses are a TG-MAS apparatus (meaning a thermo gravimetry and mass spectrometry apparatus), a TPD apparatus (meaning a temperature programmed desorption apparatus), and the like.

In the above apparatuses, a heating unit is used for heating a sample. For example, Japanese Patent Laid-Open Publication No. 4-361145 discloses, at pages 2 to 3 and in FIG. 1 thereof, a heating unit using a heater obtained by winding a heater wire around a cylindrical bobbin. In the thermal analysis apparatus using such a type of heating unit, a sample of interest has to be inserted into and removed from the inner heating region of the heating unit. For example, Japanese Patent Laid-Open Publication No. 2005-331432 discloses, at page 7 and in FIG. 2 thereof, a technique for facilitating the aforesaid inserting and removing operation for the sample. In the technique, a heating unit such as an electric furnace is moved so as to release the sample outside the heated region.

In recent years, conditions required for the thermal analysis apparatus has been diversified. More specifically, measurements under a specific environment have been required to be performed. Such a measurement may be, for example, a simultaneous measurement of the TG gas analysis and the DTA gas analysis or a measurement under a predetermined humidity atmosphere. In order to meet the diversification, many types of the heating units have been available, and a large number of accessories have been added to the heating unit. For example, tubes for carrying gas may be additionally provided to a heating unit for a gas analysis. Further, a humidity generator may be additionally provided to a heating unit for a humidity analysis. In such cases, the weight of the entire heating unit becomes large thereby to apply a large load on a mechanism for moving the heating unit. Thus, it becomes necessary to prepare a large-scaled moving mechanism capable of enduring a large load. Further, it is necessary to prepare and secure a space allowing tubes to move when the heating unit is moved. Since a conventional thermal analysis apparatus requires a large-scale moving mechanism and a space for allowing tubes or the like to move freely as mentioned above, there is a problem that the apparatus inevitably has a large-sized and a strongly-built construction.

SUMMARY OF THE INVENTION

The present invention has been made to solve the above problems, and an object thereof is to provide a thermal analysis apparatus for performing thermal analysis measurement using a temperature control unit including a heating unit, in which a mechanism for exchanging samples to be measured is easier to be made very small in structure.

A first thermal analysis apparatus according to the present invention includes: a sample temperature control unit for surrounding a sample placed on a measurement position and controlling the temperature of the sample; a sample supporting unit for supporting the sample; and a sample moving unit for allowing the sample supporting unit to slide between a first position at which the sample is situated at the measurement position and a second position at which the sample is situated at a distant position which is a position outside the sample temperature control unit.

In the above structure, the sample is placed on a predetermined position of the sample supporting unit usually in a state where it is enclosed in a vessel having a predetermined shape and capacity, although the sample can be placed by itself. The term "sample" indicates in the present specification a sample itself or a sample as encapsulated in a vessel. Therefore, "to place a sample on the sample supporting unit" denotes that a sample itself is placed on the sample supporting unit or that a vessel encapsulating a sample is placed on the sample supporting unit.

Examples of the above thermal analysis apparatus include a TG apparatus, a DTA apparatus, a DSC apparatus, a TG-DTA apparatus, and the like. In the TG apparatus, the sample supporting unit is constituted by a balance beam provided with a sample plate, on which the sample is placed. In the DTA apparatus and the DSC apparatus, the sample supporting unit is constituted by a heat transmitting structure provided with a thermosensitive plate. The sample is placed on the thermosensitive plate, and a thermocouple connected to the thermosensitive plate measures the sample temperature. In the TG-DTA apparatus, the sample supporting unit is constituted by a balance beam provided with a thermosensitive plate. The sample is placed on the thermosensitive plate, and a thermocouple connected to the thermosensitive plate measures the sample temperature.

According to the first thermal analysis apparatus having the configuration described above, when the sample is taken out of the sample temperature control unit, the sample temperature control unit is not moved but the sample supporting unit is moved. Therefore, even when the heavy sample temperature control unit including a heater unit is employed or accessories such as a tube are provided in the sample temperature control unit, a structure for performing replacement of the sample can be configured in a smaller size and in a simpler manner.

In the first thermal analysis apparatus according to the present invention, it is preferable that the distant position be a position which is deviated laterally relative to a line trajectory extending from the measurement position to the outside of the sample temperature control unit. If the distant position is present on the line trajectory extending from the sample temperature control unit, it may be difficult for the operator to perform some sort of processing for a sample section of the sample supporting unit at the distant position. Such a processing may be a replacement of the sample or maintenance of a heat-sensitive portion. On the other hand, if the distant position is set to a position deviated from the line trajectory, the operator can easily accomplish the processing. Further, even if the sample is dropped during the processing, precision devices or mechanisms within the thermal analysis apparatus are not contaminated and damaged by the sample dropped.

A second thermal analysis apparatus according to the present invention includes: a sample temperature control unit for surrounding a sample placed on a measurement position and controlling the temperature of the sample; a balance beam for supporting the sample and capable of tilting about a pivot point; and a sample moving unit for allowing the balance beam to slide between a first position at which the sample is situated at the measurement position and a second position at which the sample is situated at a distant position which is a position outside the sample temperature control unit.

The second thermal analyses apparatus is an apparatus that uses the balance beam to measure a weight change of the sample. Examples of this thermal analysis apparatus include a TG apparatus and a TG-DTA apparatus. Generally, in these apparatus, a tilt detection sensor for detecting the tilting angle of the balance beam, a beam driving mechanism for applying a rotation torque to the balance beam, and the like are additionally provided around the balance beam. In the present invention, the balance beam is moved between the first and the second positions in order to move the sample from the inside of the sample temperature control unit to the outside thereof and vice versa. At this time, various mechanisms additionally provided to the balance beam do not have to be moved together with the balance beam. However, in the case where the balance beam and mechanisms additionally provided thereto are not separable each other because of its own structural feature, the additionally provided mechanisms are moved together with the balance beam.

According to the second thermal analysis apparatus, when the sample is taken out of the sample temperature control unit, the sample temperature control unit is not moved but balance beam is moved. Therefore, even when the heavy sample temperature control unit is employed or accessories are provided in the sample temperature control unit, a structure for performing replacement of the sample can be configured in a smaller size and in a simpler manner.

In the second thermal analysis apparatus, it is preferable that the distant position be a position which is deviated laterally relative to a line trajectory extending from the measurement position to the outside of the sample temperature control unit. As a result, when an operator performs some sort of processing for the sample section at the distant position, the operator can easily accomplish the processing. Further, even if the sample is dropped during the processing, devices within the thermal analysis apparatus are not damaged by the sample dropped.

Further, it is preferable that the second thermal analysis apparatus includes a cover for surrounding the sample temperature control unit and the balance beam, and it is also preferable that the cover has an opening for taking out and putting in the sample at a portion corresponding to the distant position. The cover surrounding the sample temperature control unit and the balance beam can prevent the balance beam and the like from being exposed to air atmosphere, allowing a correct weight measurement. Further, by giving the opening to the cover corresponding to the distant position, the sample may be attached to and removed from the balance beam through the opening. This enables to exchange samples through the opening.

In the second thermal analysis apparatus, it is preferable that the sample moving unit has a liner movement unit for allowing the balance beam to linearly slide and a rotational movement unit for allowing the balance beam to rotationally slide, and it is further preferable that the distant position be a position which is deviated laterally relative to a moving path of the sample on which the sample slides linearly as driven by the linear movement unit.

In the present invention, the sample moving unit may be configured only by the linear movement unit. In this case, the distant position of the sample is defined on the line trajectory extending from the measurement position. Alternatively, the sample moving unit may be configured by a combination of the linear movement unit and the rotational movement unit. In this case, the sample supported by the balance beam may be conveyed to a position deviated from the line trajectory. Conveying the sample to such a deviated position results in the following two advantages. A first advantage is that even if the sample is dropped from the balance beam, it is possible to prevent the main mechanism of the thermal analysis apparatus from being hit and damaged by the dropped sample. The second advantage is that it is possible to move the sample near the operator, making it easy for the operator to perform replacement of the sample.

Further, in the second thermal analysis apparatus, it is preferable that the rotational movement unit includes a gear member integrated with the balance beam so as not to be rotatable relative to the balance beam and a rack immovably provided in a position at which it can engage with the gear member. By allowing the gear member and the rack to engage with each other while the balance beam slides linearly as driven by the linear movement unit, the balance beam can rotationally slide by utilizing the linearly driving force caused by the linear movement unit.

Further, in the second thermal analysis apparatus, the moving speed of the balance beam is preferably increased gradually when it starts to rotationally slide after completion of its linear slide movement and/or when it starts to linearly slide after completion of its rotational slide movement. With this configuration, a smoothly change of movement of the balance beam both from the linear slide movement to the rotational slide movement and from the rotational slide movement to the linear slide movement can be obtained, thereby to prevent the balance beam from being damaged as well as prevent the sample from being dropped from the balance beam.

Further, in the second thermal analysis apparatus, the sample moving unit preferably increases the moving speed of the balance beam gradually when the balance beam starts its sliding movement from the first position or second position and/or preferably decreases the moving speed of the balance beam gradually when the balance beam stops its sliding movement toward the first position or second position. With such a construction, the balance beam may start or stop its own sliding movement slowly and smoothly, thereby to prevent the balance beam from being damaged as well as prevent the sample from being dropped from the balance beam.

A third thermal analysis apparatus according to the present invention includes: a sample temperature control unit for surrounding a sample placed on a measurement position and controlling the temperature of the sample; a balance beam for supporting the sample and capable of tilting about a pivot point; a detection mechanism provided to the balance beam for detecting a tilt of the balance beam; a beam driving mechanism provided to the balance beam for driving the balance beam to tilt about the pivot point; a balance unit having the balance beam, the detection mechanism, and the beam driving mechanism in an integrated manner; and a sample moving unit for allowing the balance unit to slide between a first position at which the sample is situated at the measurement position and a second position at which the sample is situated at a distant position which is a position outside the sample temperature control unit.

The third thermal analysis apparatus is a thermal analysis apparatus having a structure in which a mechanism for detecting a tilt of the balance beam and a beam driving mechanism for giving a rotation moment to the balance beam are additionally provided to the balance beam. In this thermal analysis apparatus, the beam driving mechanism gives a rotation moment to the balance beam in accordance with the tilt of the balance beam detected by the tilt detection mechanism, thereby enabling a feedback control for maintaining the balance beam in a horizontal state at all times. Thus, based on the amount of an electric current applied to the beam driving mechanism during the feedback control, the tilt amount of the balance beam and hence the weight change in the sample can be calculated and obtained.

In the third thermal analysis apparatus having the configuration described above, the balance beam, the detection mechanism, and the beam driving mechanism are integrated with each other to form a balance unit, and the balance unit is allowed to slide by the sample moving unit to thereby allow the balance beam to move between the first and the second positions. According to the third thermal analysis apparatus, when the sample is taken out of the sample temperature control unit, the sample temperature control unit is not moved but the balance beam is moved. Therefore, even when a heavy sample temperature control unit is employed or accessories are provided in the sample temperature control unit, a structure for performing replacement of the sample can be configured in a small size and in a simple manner.

Also, in the third thermal analysis apparatus, the distant position is preferably a position which is deviated laterally relative to a line trajectory extending from the measurement position to the outside of the sample temperature control unit. As a result, an operator may easily perform some sort of processing for the sample section, such as a replacement of the sample or maintenance of a heat-sensitive portion, at the distant position. Further, even if the sample is dropped during the processing, precision devices or mechanisms within the thermal analysis apparatus are not contaminated or damaged by the sample dropped.

A fourth thermal analysis apparatus according to the present invention includes: a protective tube for surrounding a sample placed on a measurement position; a heat application unit provided around the protective tube for heating the inside of the protective tube; a balance beam capable of tilting about a pivot point while supporting the sample; a detection mechanism provided to the balance beam for detecting a tilt of the balance beam; a beam driving mechanism provided to the balance beam for allowing the balance beam to tilt about the pivot point; a balance unit having a housing in which the pivot point, the detection mechanism, the beam driving mechanism, and portions of the balance beam that correspond to the pivot point, the detection mechanism, the beam driving mechanism are contained; and a sample moving unit for allowing the balance unit to slide between a first position at which the sample is situated at the measurement position and a second position at which the sample is situated at a distant position which is a position outside the sample temperature control unit, wherein when the balance unit is situated at the first position, the protective tube and the housing are connected to each other in an air-tight manner.

The fourth thermal analysis apparatus is a thermal analysis apparatus including a balance unit, which containing (1) the tilt detection mechanism for the balance beam, (2) the driving mechanism for the balance beam, (3) the portion at which the balance beam is supported, and (4) portions of the balance beam that corresponds to the tilt detection mechanism and the driving mechanism. A portion of the balance beam at which the sample is supported and the vicinity thereof protrude from the housing. In the thermal analysis apparatus having the above configuration, the entire balance unit including the housing is allowed to slide by the sample moving unit to thereby allow the balance beam to move between the first and the second positions.

According to the fourth thermal analysis apparatus, when the sample is taken out of the sample temperature control unit, the sample temperature control unit is not moved but the balance beam is moved. Therefore, even when a heavy sample temperature control unit is employed or accessories are provided in the sample temperature control unit, a structure for performing replacement of the sample can be configured in a small size and in a simple manner.

BRIEF DESCRIPTION OF THE DRAWINGS

FIG. 1A is a perspective view showing the entire structure of an embodiment of a thermal analysis apparatus according to the present invention, and FIG. 1B is a perspective view showing a pullout table mounted in and pulled out of a cover portion of an operating section;

DETAILED DESCRIPTION OF THE PREFERRED EMBODIMENTS

Figure 2:
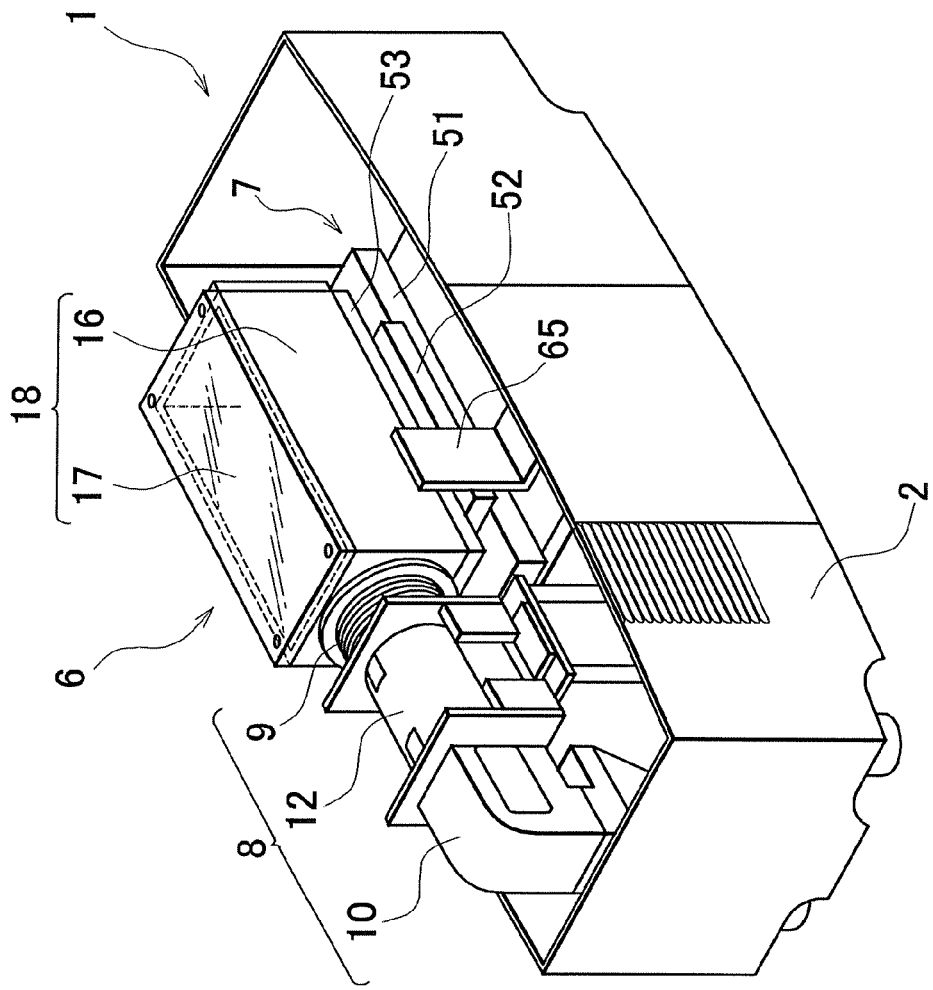
FIG. 2 is a perspective view showing the thermal analysis apparatus of FIG. 1A as the upper cover thereof is removed.

A thermal analysis apparatus according to the present invention will be described based on an embodiment. It should be noted that the present invention is not limited to the following embodiment. While the present invention is described below by referring to the accompanying drawings, the components may be shown in the drawings with dimensional ratios that differ from the actual ratios for the purpose of clearly showing characteristic parts thereof.

FIG. 1A shows the entire structure of a TG-DTA apparatus, which is an example of a thermal analysis apparatus according to the present invention. In FIG. 1A, the thermal analysis apparatus 1 has a main body cover 2, three covers 3a, 3b, and 3c fitted to the upper side of the main body cover 2, and an operating section cover 4 fitted to the portion which is on the front side of the covers 3a to 3c and on the upper side of the main body cover 2. Devices used for performing thermal analysis are stored in an inner space surrounded by the above covers 2, 3a to 3c, and 4. These covers are made of metal, synthetic resin, or the like. The coupling between these covers is realized by an arbitrary coupling technique, such as a technique with a screw clamp or an engaging technique in which a pair of engaging members are engaged with each other.

Figure 3:
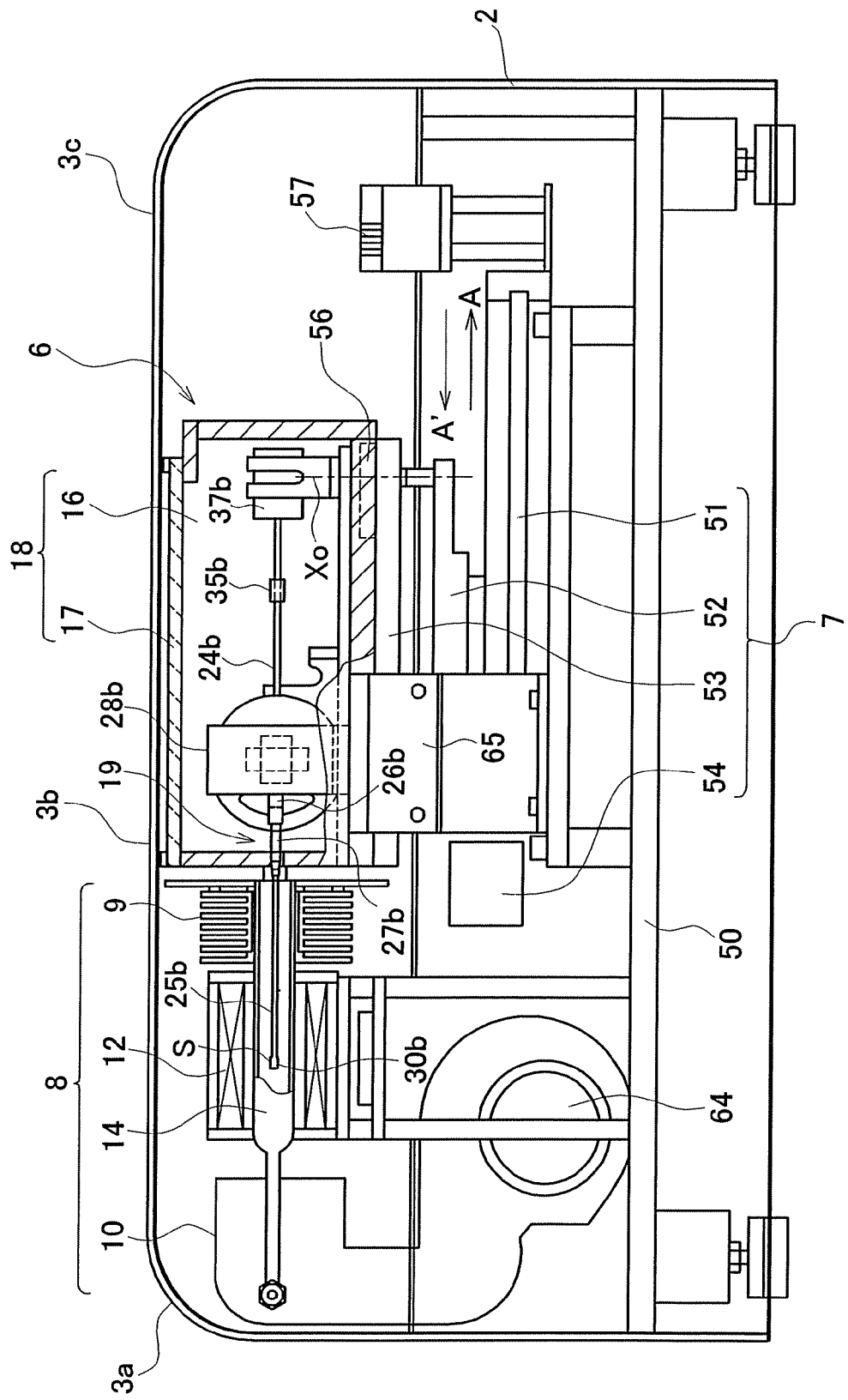
FIG. 3 is a cross-sectional front view of the thermal analysis apparatus of FIG. 2.
Figure 4:
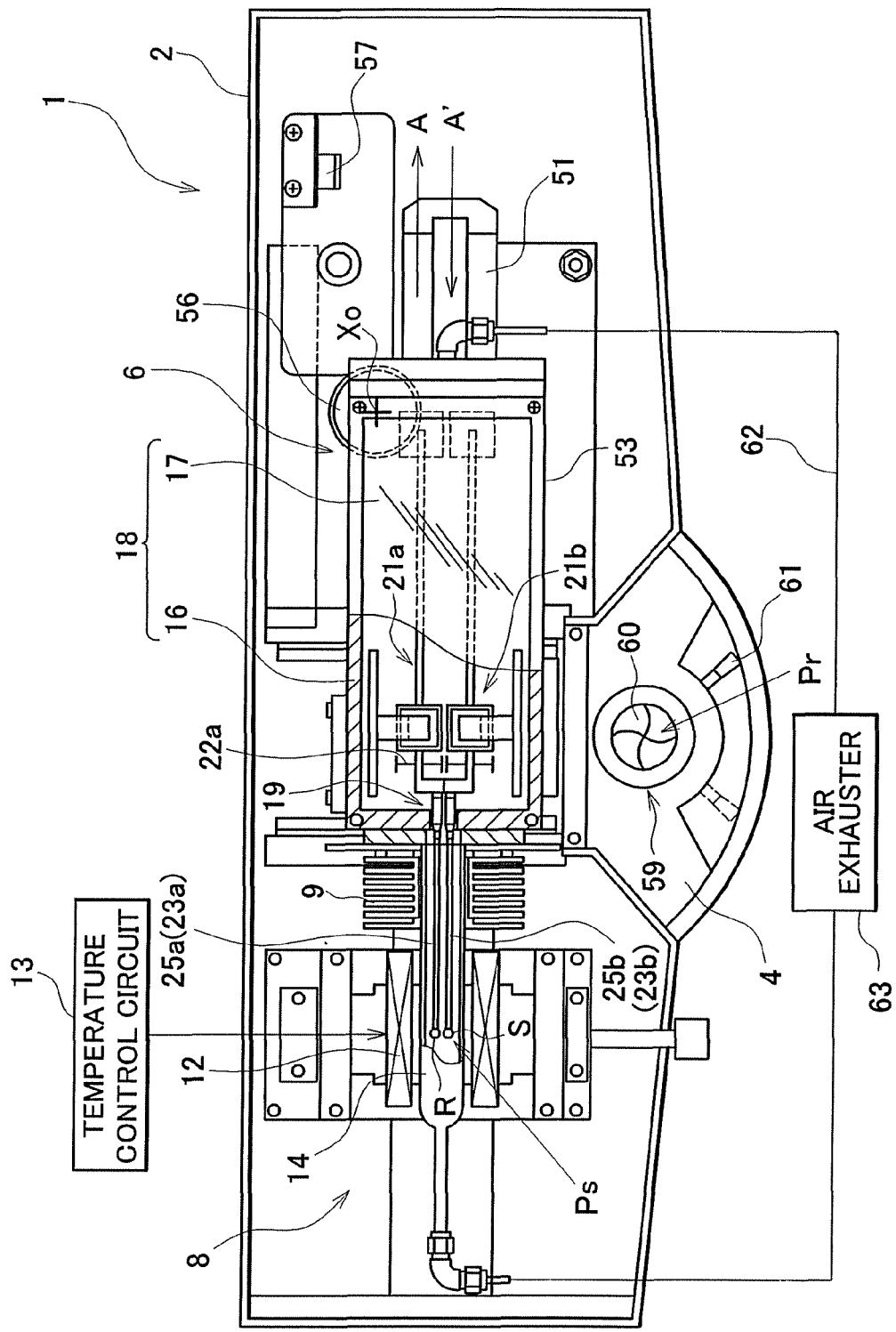
FIG. 4 is a cross-sectional plan view of the thermal analysis apparatus of FIG. 2.

FIG. 2 shows the thermal analysis apparatus 1 of FIG. 1A in a state where the upper covers 3a, 3b, 3c and the operating section cover 4 have been removed therefrom. FIG. 3 shows a longitudinally sectional structure of the thermal analysis apparatus 1 as viewed from its front side. FIG. 4 shows a transversely sectional structure of the thermal analysis apparatus 1 as viewed from above. In FIG. 2, a balance unit 6, a sample moving unit 7, and a sample temperature control unit 8 are mounted inside the cover 2.

The sample temperature control unit 8 has, as shown in FIGS. 3 and 4, a protective tube 14, a heater 12, a cooling fin 9, and an air duct 10. The heater 12 functions as a heater unit for heating a sample S and a reference substance R. The cooling fin 9 and the air duct 10 jointly function as a cooling unit for cooling the sample temperature control unit 8. The cooling fin 9 also cools the sample S and the like. The heater 12 is formed by, for example, winding a heater wire around a cylindrical heater bobbin. As shown in FIG. 4, a temperature control circuit 13 is connected to the heater wire of the heater 12. The temperature control circuit 13 controls an electric current to be supplied to the heater wire of the heater 12 according to a temperature control program stored in the circuit itself or a temperature control program stored in a host computer (not shown).

The protective tube 14 is made of, for example, ceramic and formed into a cylindrical shape. The protective tube 14 is mounted within the heater 12. The main function of the protective tube 14 is to protect the heater 12 from a gas generated from the sample S. The right side portion of the protective tube 14 is a large-diameter cylindrical portion, and the left side thereof is a small-diameter cylindrical portion. The large-diameter portion of the protective tube 14 is housed in the inner heating area of the heater 12. The protective tube 14 extends outside the heater 12 at its right side, and the cooling fin 9 is disposed around the portion of the protective tube 14 protruded from the heater 12. The right end surface of the protective tube 14 is opened.

The balance unit 6 has a housing 18 constructed by fixing a plate-shaped transparent cover 17 to the upper surface of a box-formed base body 16 by means of an arbitrary position-fixing method such as screwing. The housing-base body 16 is made of metal or synthetic resin. The transparent cover 17 is made of, for example, synthetic resin having a characteristic of allowing light to pass through itself. An opening 19 for allowing the passage of a balance beam is formed in substantially the center of the side plate on the left side of the housing-base body 16. The housing 18 is formed into an airtight structure, excluding the portion of the opening 19. Although described in detail later, the reason for forming the top of the housing 18 using the transparent cover 17 is that replacement of the balance beam, which is performed by an operator at the portion of the opening 19, is enabled without removal of the upper cover of the housing 18.

Figure 5:
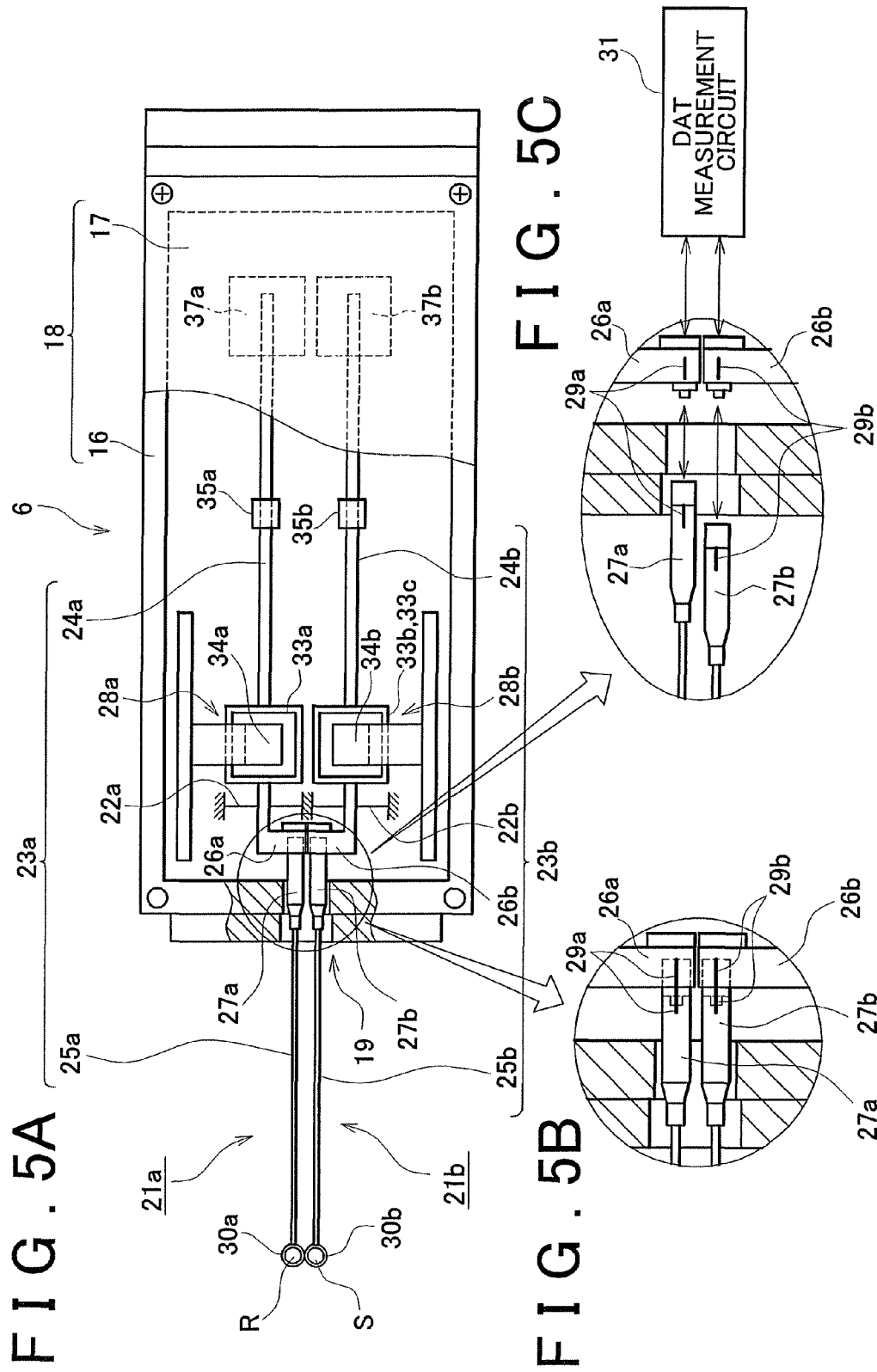
FIG. 5A is a cross-sectional plan view of a balance unit which is a main part of the thermal analysis apparatus of FIG. 4, and FIGS. 5B and 5C are cross-sectional plan views showing the main part of a balance beam in an enlarged manner.
Figure 6:
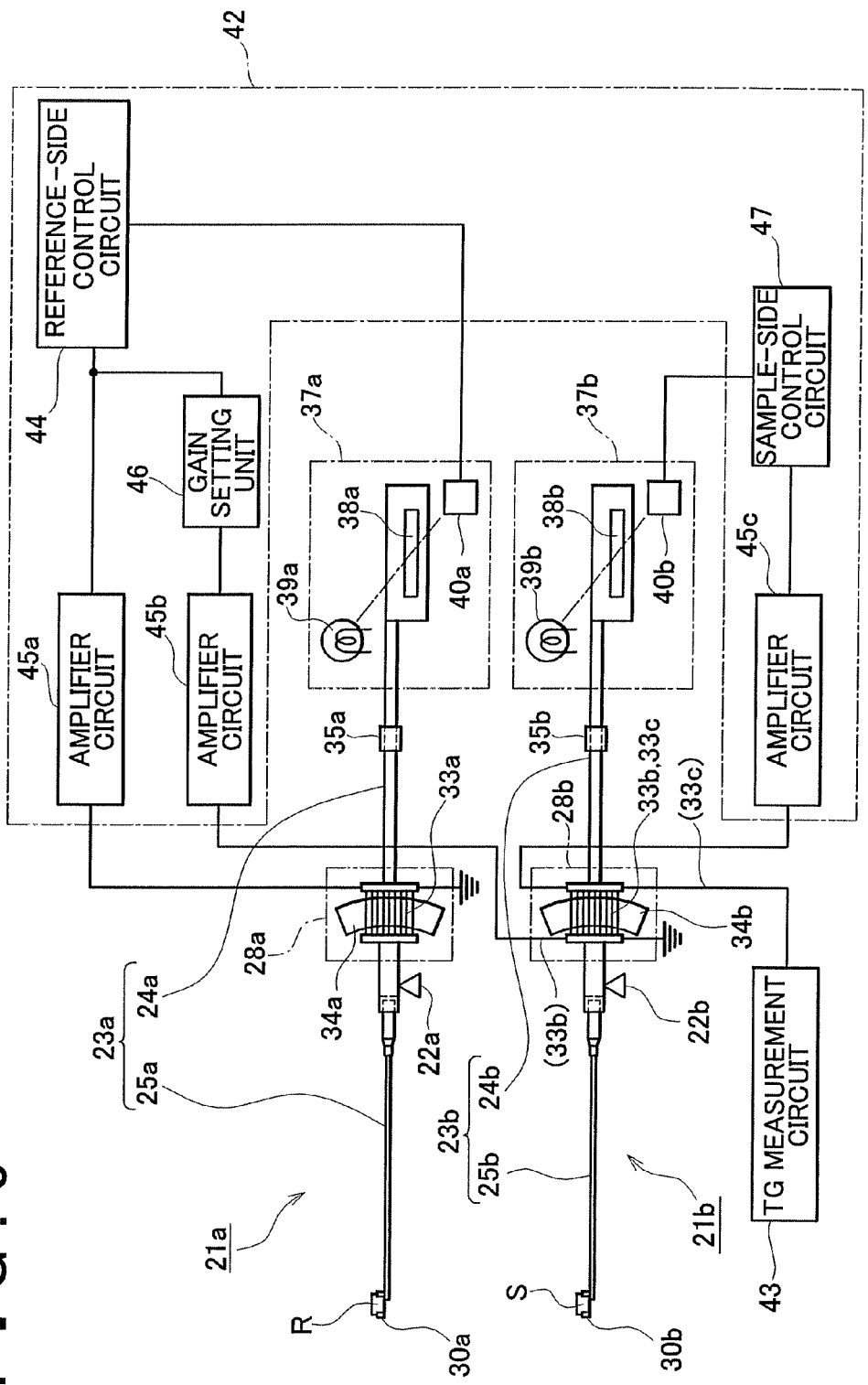
FIG. 6 is a view showing a side-view structure of the balance unit of FIG. 5 and an electric circuit associated with the balance unit.

FIG. 5A shows the structure of the balance unit 6 as taken a plane view thereof. FIG. 6 shows the structure of a balance mechanism mounted within the balance unit 6 as taken a side view and an electric circuit associated with the balance mechanism. Although one of two balance mechanisms located on the back side cannot actually be seen because it is arranged behind the front side balance mechanism in FIG. 6, the two balance mechanisms are arranged up and down for descriptive purposes.

In FIG. 5A, two balance mechanisms, that is, a reference-side balance mechanism 21a and a sample-side balance mechanism 21b are mounted inside the housing 18. The balance mechanisms 21a and 21b have balance beams 23a and 23b, respectively, which are supported by torsion wires 22a and 22b for pivotal movement. The torsion wires 22a and 22b, hereinafter, may be referred to merely as pivot points. The balance beams 23a and 23b are constructed by connecting second beams 25a and 25b to first beams 24a and 24b supported by the torsion wires 22a and 22b.

L-shaped socket portions 26a and 26b are provided at the left ends of the first beams 24a and 24b, respectively. Plug portions 27a and 27b are provided at the right ends of the second beams 25a and 25b, respectively. The plug portions 27a and 27b are inserted into the socket portions 26a and 26b as shown in FIGS. 5B and 5C to allow the first beams 24a, 24b and second beams 25a, 25b to be coupled to each other, thus forming the balance beams 23a and 23b. In the present embodiment, the sample-side balance beam 23b serves as a sample supporting unit for supporting the sample S. Marks denoted by reference numerals 29a and 29b in FIGS. 5B and 5C are confirmation marks for confirming the attachment angle of the plug portions 27a and 27b to the socket portions 26a and 26b.

In FIG. 5A, sample plates 30a and 30b are fixed to the leading end of the second beams 25a and 25b. A thermosensitive plate is generally used in the TG-DTA apparatus as a sample plate, and therefore, the sample plate may hereinafter be referred to as a thermosensitive plate. A reference substance R being stable in a thermal change is placed on the reference-side thermosensitive plate 30a, and a sample S to be measured is placed on the sample-side thermosensitive plate 30b. It should be noted that both the reference substance R and sample S are placed on the thermosensitive plates 30a and 30b with the substance and the sample being enclosed in vessels having a predetermined shape. Although detailed illustration is omitted, a plurality of thermocouple wires forming a thermocouple are fixed to the bottom surfaces of the thermosensitive plates 30a and 30b by welding, and the like. The thermocouple wires extend through the inside of the second beams 25a and 25b to the plug portions 27a and 27b to form terminals for electrical connections. On the other hand, a DTA measurement circuit 31 is connected to the socket portions 26a and 26b. Input/output lines starting from the DTA measurement circuit 31 extend to the socket portions 26a and 26b to form terminals for electrical connections. The DTA measurement circuit 31 is, in FIG. 2, provided in an appropriate location within a space surrounded by the cover 2.

The insertion of the plug portions 27a and 27b into the socket portions 26a and 26b causes their inner terminals to electrically be connected to each other, allowing the thermocouple wires extending from the thermosensitive plates 30a and 30b to be connected to the input/output port of the DTA measurement circuit 31. The DTA measurement circuit 31 detects a change of temperature difference of the sample-side thermosensitive plate 30b relative to the reference-side thermosensitive plate 30a with respect to a time lapse. The detected change of temperature difference gives an occurrence of a thermal change in the sample S. The structure for connecting the plug portions 27a, 27b and the socket portions 26a, 26b may be the structure disclosed in Japanese Patent Laid-Open Publication No. 8-184545.

When the plug portions 27a, 27b is fitted to the socket portions 26a, 26b, respectively, the first beams 24a, 24b and the second beams 25a, 25b are connected to each other, thus forming the balance beams 23a, 23b. Further, removing the plug portions 27a, 27b from the socket portions 26a, 26b, respectively, separates the first beams 24a, 24b and the second beams 25a, 25b. Separation and connection of the first beams 24a, 24b and the second beams 25a, 25b are carried out mainly for exchanging the second beams 25a, 25b. Operators need to perform the exchange of the second beams 25a and 25b while viewing the plug and socket portions. In the present embodiment, the upper cover 17 of the housing 18 is made of a transparent member, so that operators can perform the exchange of the second beams 25a and 25b while viewing the plug and socket portions without removing the upper cover 17 from the housing base body 16. This is very convenient.

In FIG. 6, a first electromagnetic coil 33a is provided near the pivot point 22a of the first beam 24a of the reference-side balance beam 23a. A magnet 34a penetrates the first electromagnetic coil 33a. A second electromagnetic coil 33b and a third electromagnetic coil 33c are provided near the pivot point 22b of the first beam 24b of the sample-side balance beam 23b. The second electromagnetic coil 33b and the third electromagnetic coil 33c are wound separately around one side and the other side of a single coil bobbin. Alternatively, they may be wound around a single coil bobbin in an overlapped manner. A magnet 34b penetrates both the second and third electromagnetic coils 33b and 33c. The magnets 34a and 34b are fixed to the housing base body 16 as seen from FIG. 5A.

In FIG. 6, the first electromagnetic coil 33a and the magnet 34a function together as a beam driving unit 28a for tilting the balance beam 23a about the pivot point 22a. Further, the second and the third electromagnetic coils 33b, 33c, and the magnet 34b function together as a beam driving unit 28b for tilting the balance beam 23b about the pivot point 22b. The balance weights 35a and 35b are fixed with screws on a suitable position of the first beams 24a and 24b so as to be changeable in position. By appropriately controlling the position of the balance weights 35a and 35b on the beams, the balance beams 23a and 23b are set to an initial position where they keep their balance.

Tilt detection mechanisms 37a and 37b are provided at the right end of the first beams 24a and 24b, respectively. The tilt detection mechanisms 37a and 37b have slits 38a, 38b formed at the rear ends of the first beams 24a, 24b, light sources 39a, 39b disposed in one sides of the slits 38a, 38b, and light-sensitive elements 40a, 40b disposed in the other sides of the slits 38a, 38b. The light sources 39a and 39b may be, for example, a light emitting diode, respectively. The light emitting diode may be referred to as "LED" hereafter. The light-sensitive elements 40a and 40b may be, for example, a photodiode, respectively.

A feedback control circuit 42 is provided between the tilt detection mechanisms 37a, 37b and beam driving units 28a, 28b. The feedback control circuit 42 controls the balance beams 23a and 23b, respectively, to maintain a horizontal state. The third electromagnetic coil 33c has terminals at an upstream side and a downstream side with respect to flow of an electric current. A TG measurement circuit 43 is connected to the downstream side terminal of the third electromagnetic coil 33c. The TG measurement circuit 43 calculates a weight change occurring in the sample S based on the value of an electric current flowing through the third electromagnetic coil 33c. The feedback control circuit 42 and the TG measurement circuit 43 are, in FIG. 2, provided in appropriate locations within a space surrounded by the cover 2.

The feedback control circuit 42 and the TG measurement circuit 43 may employ the same structure of circuit as that disclosed in Japanese Patent Laid-Open Publication No. 8-292142. These circuits will briefly be described below. The feedback control circuit 42 has a reference-side control circuit 44 connected to the output terminal of the light-sensitive element 40a in the reference-side balance mechanism 21a. The reference-side control circuit 44 includes, for example, a proportional-integral derivative circuit, which may be referred to as "PID circuit". The output of the reference-side control circuit 44 is separately taken in a parallel circuit. In one of the parallel circuit, the output of the reference-side control circuit 44 is transmitted to the input terminal of the first electromagnetic coil 33a within the beam driving unit 28a on the side of the reference-side balance mechanism 21a through an amplifier circuit 45a. In the other of the parallel circuit, the output of the reference-side control circuit 44 is transmitted to the input terminal of the second electromagnetic coil 33b within the beam driving unit 28b on the side of the sample-side balance mechanism 21b through a gain setting unit 46 and an amplifier circuit 45b.

The feedback control circuit 42 further has a sample-side control circuit 47 connected to the output terminal of the light-sensitive element 40b within the sample-side balance mechanism 21b. The sample-side control circuit 47 also includes, for example, a PID circuit. The output signal of the sample-side control circuit 47 is transmitted to the input terminal of the third electromagnetic coil 33c within the beam driving unit 28b on the side of the sample-side balance mechanism 21b through an amplifier circuit 45c. The TG measurement circuit 43 is connected to the output terminal of the third electromagnetic coil 33c. The TG measurement circuit 43 calculates a weight change occurring in the sample S based on the value of an electric current flowing through the third electromagnetic coil 33c.

When the balance beam 23a within the reference-side balance mechanism 21a tilts because of some reason, the position of the slit 38a is changed to change the amount of light received by the light-sensitive element 40a, resulting in change of the output signal of the light-sensitive element 40a. The reference-side control circuit 44 generates a compensation signal based on the change of the output signal of the light-sensitive element 40a and outputs it to the first electromagnetic coil 33a within the reference-side beam driving unit 28a through the amplifier circuit 45a. As a result, an electric current flows through the first electromagnetic coil 33a, allowing interaction between the coil 33a and the magnet 34a to generate a force. This force generates a rotation moment in the direction opposite to the tilt of the balance beam 23a to compensate the tilt, thus maintaining the horizontal state of the reference-side balance beam 23a.

The compensation signal output from the reference-side control circuit 44 is also supplied to the second electromagnetic coil 33b within the sample-side beam driving unit 28b through the gain setting unit 46 and the amplifier circuit 45b. As a result, the same amount of compensation moment as that for the reference-side balance beam 23a is given to the sample-side balance beam 23b. In addition, in the sample-side balance mechanism 21b, the output signal of the light-sensitive element 40b changes with the tilt of the balance beam 23b and, correspondingly, the sample-side control circuit 47 generates a compensation signal and outputs it to the third electromagnetic coil 33c within the sample-side beam driving unit 28b through the amplifier circuit 45c. As a result, an electric current flows through the second electromagnetic coil 33b and the third electromagnetic coil 33c both within the sample-side beam driving unit 28b, allowing interaction between the coils 33b, 33c and magnet 34b to generate a force. This force generates a rotation moment in the direction opposite to the tilt of the balance beam 23b to compensate the tilt, thus maintaining the horizontal state of the sample-side balance beam 23b. A weight change occurring in the sample S is calculated by the TG measurement circuit 43 based on the value of an electric current which has flowed through the third electromagnetic coil 33c.

In the present embodiment, a compensation signal for the tilt of the reference-side balance beam 23a is fed back not only to the reference-side balance beam 23a itself but to the sample-side balance beam 23b. Thus, when the two balance beams are influenced by a factor other than the weight change occurring in the sample S, it is possible to prevent unnecessary noise from occurring in a transitional control state immediately after that, enabling the TG measurement with high reliability.

In FIG. 5A, portions that are the pivot points 22a, 22b, the tilt detection mechanisms 37a, 37b, and the beam driving units 28a, 28b, as well as portions of the balance beams 23a and 23b that correspond respectively to the above portions are housed in the housing 18. Note that such portions of the balance beams 23a and 23b that correspond respectively to the above portions coincide substantially with the first beams 24a and 24b. Portions of the balance beams 23a and 23b other than the above mentioned portions, that are substantially equal to the second beams 25a and 25b, extend outside the housing 18 through the opening 19 formed in the side plate of the housing 18.

In the present embodiment, the operator performs a replacement of the sample S supported by the sample-side balance mechanism 21b, after the balance unit 6 is moved and the sample S is taken out of the protective tube 14 of FIG. 4. Hereinafter, a configuration that allows such movement of the balance unit 6 will be described.

In FIG. 3, the sample moving unit 7 is provided below the housing 18. The sample moving unit 7 has a rail 51 fixed to a frame 50, a slider 52 sliding along the rail 51, and a unit base plate 53 fixed on the slider 52. The housing base body 16 of the housing 18 is provided on the unit base plate 53 in such a manner as to be rotationally moved about an axial line X0 passing through the center of a gear member 56 provided at the rear side of the housing 18 and extending vertically. A structure for rotatably setting the housing base body 16 on the base plate 53 as described above can be arbitrarily selected. Specifically, for example, the housing base body 16 and the base plate 53 are rotatably coupled to each other through a shaft member provided on the axial line X0. Alternatively, the housing base body 16 is guided with an appropriate guide member so as to be rotated on the base plate 53 about the axial line X0.

In FIG. 3, the sample moving unit 7 includes an electric motor 54 capable of controlling the output rotational velocity. The motor may be, for example, a pulse motor or a stepping motor. The output shaft of the motor 54 is coupled to the slider 52 for transmitting a drive force. When the motor 54 is activated to rotate its output shaft, the slider 52 slides along the rail 51. Such a slider mechanism may be achieved by a mechanism in which, for example, a screw shaft is fixed to the output shaft of the motor 54, the slider 52 is equipped with a female thread capable of engaging with a male thread of the screw shaft, and the male thread and the female thread are engaged with each other. The rail 51 extends linearly and, accordingly, the slider 52 slides linearly in the horizontal direction of FIG. 3, as denoted by arrows A-A'. When the slider 52 slides, the housing 18 fixed to the slider 52 also slides integrally therewith.

FIGS. 3 and 4 show the housing 18 as being situated at the leftmost position in the A'-direction. In this state, the left side plate of the housing 18 is brought into contact with the right end surface of the protective tube 14, and the right side opening of the protective tube 14 and an opening 19 of the left-side side plate of the housing base body 16 communicate with each other. As shown in FIG. 4, the reference substance R supported by the balance beam 23a of the reference-side balance mechanism 21a and the sample S supported by the balance beam 23b of the sample-side balance mechanism 21b in the housing 18 are situated inside the protective tube 14, that is inside the heater 12.

The position of the sample S situated within the heater 12 as described above is defined as a measurement position Ps of the sample S. Further, the position of the sample-side balance beam 23b at which the sample S is situated at the measurement position Ps is defined as a first position of the sample-side balance beam 23b. In the following description, the position of the reference substance R at the time when the sample S is situated at the measurement position Ps may be referred to as a measurement position of the reference substance R. Further, the position of the reference-side balance beam 23a at which the reference substance R is situated at the measurement position may be referred to as a first position of the balance beam.

A pipe 62 is provided between the left end of the small-diameter portion of the protective tube 14 and the right side wall of the housing base body 16. An air exhauster 63 is provided on the pipe 62. The air exhauster 63 may be, for example, an air exhaust pump. When the sample-side balance mechanism 21b or the like is situated in the aforesaid first position, the left-side side wall of the housing base body 16 and the right side opening of the protective tube 14 are connected to each other in an air-tight manner. By activating the air exhauster 63 under such an air-tight condition, the insides of the protective tube 14 and the housing 18 can be formed into a vacuum or a decompressed atmosphere. Evacuating the inside of the protective tube 14 and the housing 18 is carried out in order to enable of measuring the thermal characteristics of the sample S in a vacuum, or to enable of replacing the current atmosphere within the protective tube 14 and the housing 18 with an another intended gas atmosphere.

In the thermal analysis apparatus 1 according to the present embodiment, a weight change in the sample S relative to the reference substance R is measured with the balance mechanisms 21a and 21b being situated in the first positions and the inside of the protective tube 14 being set in a vacuum as occasion demands, while the reference substance R and the sample S are heated by the heater 12 to increase their temperature according to a predetermined temperature rising program.

Figure 7:
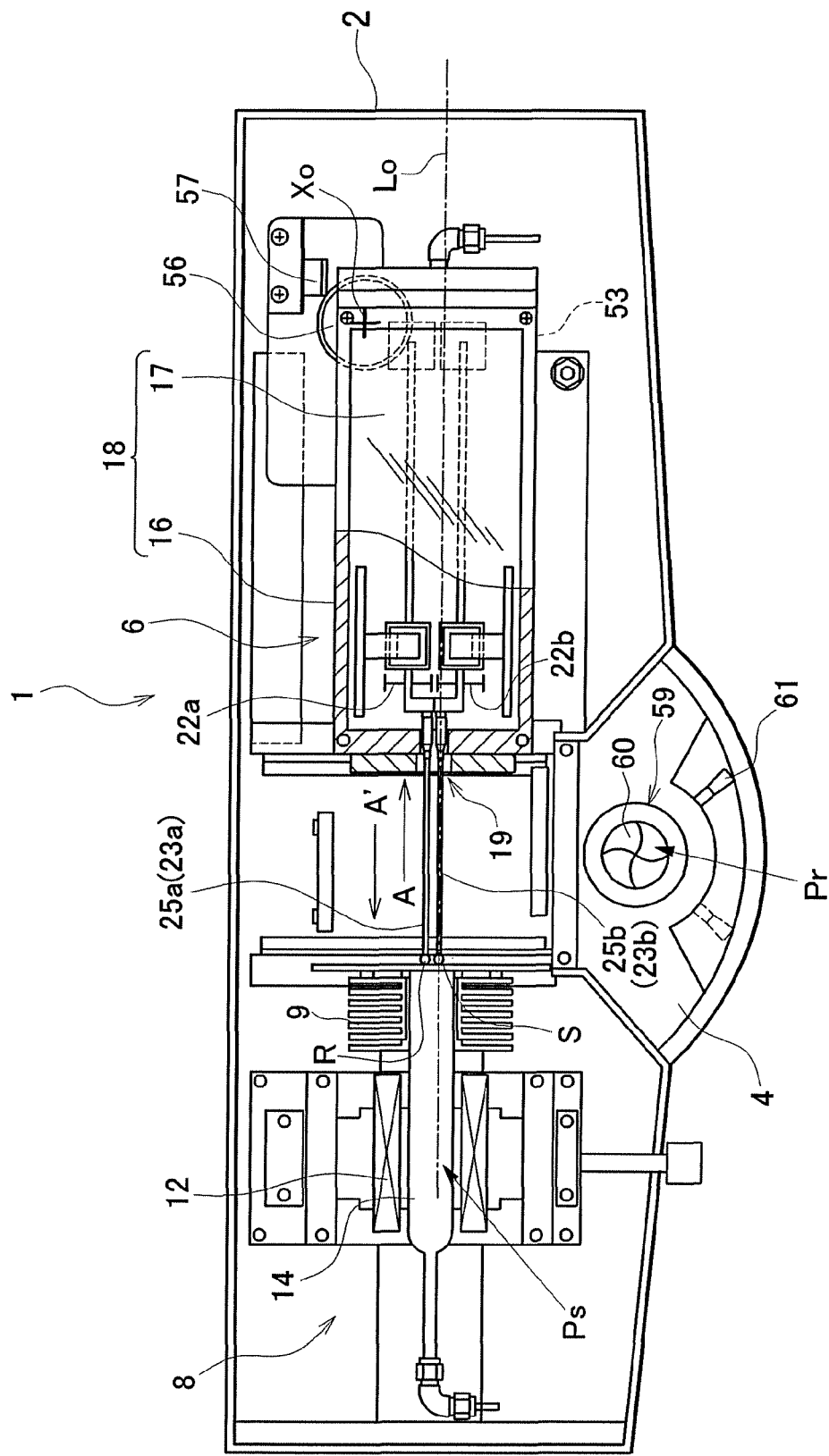
FIG. 7 is a view showing a state of movement of the structure shown in FIG. 4.

When the sample moving unit 7 is activated in FIG. 3 and thereby the housing 18 linearly slides in the direction of the arrow A (that is, the right direction), the housing 18 linearly slides in the direction shown by the arrow A in FIG. 7 along a line trajectory L0 to allow the left side plate of the housing base body 16 to be away from the right end surface of the protective tube 14 as illustrated in FIG. 7. When the housing 18 slides by a distance longer than the length of each of the second beams 25a and 25b, the reference substance R and the sample S supported by the leading ends of the beams 25a and 25b are taken out of the protective tube 14, that is, the sample temperature control unit 8.

The above-mentioned gear member 56 is provided at the side surface and the rear end of the bottom plate of the housing base body 16. The gear member 56 protrudes partially from the housing base body 16. The gear member 56 is fixed to the housing base body 16 so as not to be rotatable. A rack 57 is immovably provided at the right corner inside the cover 2. The tooth surface of the rack 57 is situated on the linear movement path of the tooth surface of the gear member 56. Accordingly, when the housing 18 linearly slides by a predetermined distance in the direction of the arrow A, the tooth surface of the gear member 56 can engage with the tooth surface of the rack 57.

The gear member 56 is fixed to the housing base body 16 so as not to be rotatable relative to the housing base body 16, and further, the bottom plate of the housing base body 16 is rotatable relative to the base plate 53 about the axial line X0. Therefore, when the housing 18 further linearly slides in the direction of the arrow A (that is, the right direction) after the gear member 56 and the rack 57 have been engaged with each other, the housing 18 rotationally slides relative to the unit base plate 53 about the axial line X0 in the direction of an arrow B (that is, in the counter-clockwise direction), as shown in FIG. 8.

Figures 8A, 8B:
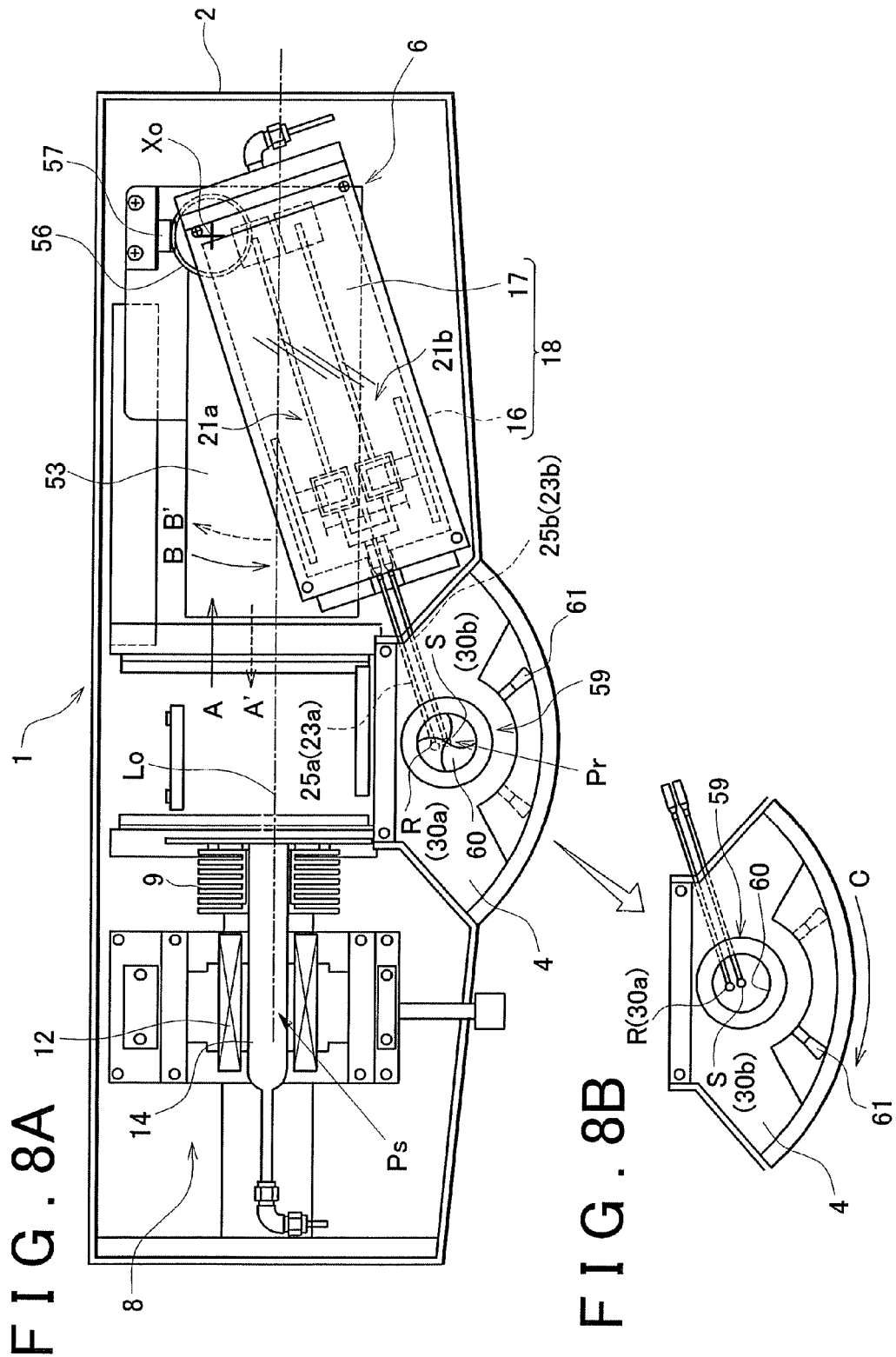
FIG. 8A is a view showing another state of movement of the structure shown in FIG. 4.
FIG. 8B is a view showing an open-close shutter as opened in an opening portion.

After the housing 18 has slid rotationally by a predetermined angle in the counter-clockwise direction in FIG. 8A, both the reference substance R supported by the balance beam 23a of the reference-side balance mechanism 21a in the housing 18 and the sample S supported by the balance beam 23b of the sample-side balance mechanism 21b in the housing 18 are situated outside the protective tube 14, that is outside the sample temperature control unit 8. More specifically, the sample S is situated at the position deviated laterally (downwardly in FIG. 7) from the line trajectory denoted by the arrow L0 in FIG. 7. The position of the sample S situated outside the sample temperature control unit 8 as mentioned above is defined as a distant position Pr. Further, the position of the sample-side balance beam 23b at which the sample S is situated at the distant position Pr is defined as a second position of the balance beam. Although the distant position Pr can be set on the line trajectory L0 as the case may be, it is set in the position deviated laterally from the line trajectory L0 in the present embodiment.

When the sample-side balance beam 23b is situated at the second position, both the sample S supported at the distant position Pr while being supported by the sample-side balance beam 23b and the reference substance R supported by the reference-side balance beam 23a are situated in the operating section cover 4. An opening 59 is formed at a portion of the upper surface of the operating section cover 4 in facing relation the reference substance R and the sample S. Although the opening 59 may merely be a simple opening, the opening 59 according to the present embodiment is provided with an opening and closing shutter 60. The opening and closing shutter 60 is interlocked with a sliding knob 61 provided on the front of the operating section cover 4. When the knob 61 is set to a closing position on the right side, the shutter 60 is closed. On the other hand, when the knob 61 is set to an opening position on the left side shown in FIG. 8B, the shutter 60 is opened. When the shutter 60 is opened with the sample-side balance beam 23b being situated at the second position, an operator may view the reference substance R and the sample S through the opening 59. In this state, an operator can exchange samples S with an exchanging tool such as tweezers. Further, the operator can perform replacement of the reference substance R according to the need.

As is clear from the description described above, the sample moving unit 7 of FIG. 3 can make both the reference-side balance mechanism 21a and the sample-side balance mechanism 21b of FIG. 4 slide from the first position shown in FIG. 4 to the second position shown in FIG. 8A. Thereafter, the unit base plate 53 is driven to slide linearly in the direction of the arrow A' with the sample-side balance mechanism 21b or the like being situated at the second position of FIG. 8A. At this time, the gear member 56 and the rack 57 cooperate to make the balance unit 6 slide rotationally in the direction of the arrow B'. Later, when the sample S reaches the position on the line trajectory L0 as shown in FIG. 7, the balance unit 6 starts to slide linearly in the direction of the arrow A' following the slide movement of the base plate 53 and, finally, reaches the first position shown in FIG. 4. In the first position of the balance unit 6 the TG-DTA measurement can be performed for the sample S.

In FIG. 3, a blower fan 64 is set in the left end area of the internal space of the cover 2. The air supply port of the blower fan 64 is connected to the air duct 10. When the blower fan 64 is activated, air is supplied from the air duct 10 to the heater 12 to thereby forcibly cool the heater 12. The cooling fin 9 assists the cooling processing for the heater 12. This cooling processing is not performed during the thermal analysis measurement but performed for cooling the sample temperature control unit 8 as soon as possible after the measurement. A guide member 65 provided opposite to the side surface of the housing base body 16 guides the linear slide movement of the housing 18 in the direction of arrows A and A'.

Operation of the thermal analysis apparatus 1 having the configuration described above will be described below.

In FIG. 8A, the balance unit 6 is set at the illustrated second position. In this state, the thermosensitive plate 30b arranged at the leading end of the sample-side balance beam 23b is situated at the distant position Pr which is a position outside the sample temperature control unit 8. The distant position Pr in this case is positioned below the opening 59 of the operating section cover 4. At this time, the thermosensitive plate 30a arranged at the leading end of the reference-side balance beam 23a is also situated below the opening 59. When the knob 61 is slid to open the shutter 60 of the opening 59 (see FIG. 8B), the thermosensitive plates 30a and 30b can be viewed through the opening 59. Therefore, an operator can place a reference substance R and a sample S on the thermosensitive plates 30a and 30b, respectively, with tweezers.

Then, a start button arranged at a predetermined position is depressed after the shutter 60 is closed. When the start button is depressed, the motor 54 of the sample moving unit 7 of FIG. 3 is activated to allow the unit base plate 53 of FIG. 8A to linearly slide in the direction of the arrow A'. At this time, the balance unit 6 to rotationally slide on the base plate 53 in the direction of the arrow B' because of the effect of the engagement of the gear member 56 and rack 57, resulting in reaching the position at which the sample S is situated on the line trajectory L0, as shown in FIG. 7

Thereafter, the unit base plate 53 successively slides linearly in the direction of the arrow A', and the balance unit 6 follow it to move in the direction of the arrow A', too. This movement allows the reference substance R supported by the reference-side balance beam 23a and sample S supported by the sample-side balance beam 23b to be inserted into the protective tube 14. Finally, the reference-side balance beam 23a and the sample-side balance beam 23b within the balance unit 6 move to their first positions shown in FIG. 4 and stop there. In this state, the reference substance R and the sample S are situated at their measurement positions Ps inside the heater 12 of the sample temperature control unit 8.

Subsequently, the temperature control circuit 13 allows the heater 12 to generate heat according to a predetermined temperature rising program to thereby heat the reference substance R and the sample S. When physical properties of the sample S change to thereby change the weight of the sample S during such a heating process, a difference in the tilt angle occurs in FIG. 6 between the sample-side balance beam 23b supporting the sample S and the reference-side balance beam 23a supporting the reference substance R whose physical properties do not change. The feedback control circuit 42 and the TG measurement circuit 43 measures a weight change of the sample S based on the difference of the tilt angle. At the same time, the temperature change in the sample S relative to the reference substance R is measured by the DTA measurement circuit 31 of FIG. 5A. As a result, measurement data based on which a TG-DTA diagram is drawn is obtained.

After completion of measurement, the corresponding information is displayed on a display device (not shown) provided in an appropriate position in the thermal analysis apparatus 1 of FIG. 1A. The operator confirms this information and operates a button (not shown) to instruct execution of processing for collecting the sample S. The motor 54 of FIG. 3 is correspondingly activated to allow the balance unit 6 to linearly slide in the direction of the arrow A. After the balance unit 6 has traveled a predetermined distance, the reference substance R and the sample S come out of the protective tube 14 as shown in FIG. 7. Thereafter, the balance unit 6 continues to slide linearly to make the gear member 56 and the rack 57 engage with each other. Then, the balance unit 6 rotationally slides in the direction of the arrow B by virtue of engagement of the gear member 56 and the rack 57, resulting in allowing the reference-side balance beam 23a and the sample-side balance beam 23b to reach their second positions shown in FIG. 8A.

When the balance beams 23a and 23b are situated at the second positions, the reference material R and the sample S supported by the balance beams 23a and 23b are situated at the position (that is, the distant position Pr) below the opening 59 of the operating section cover 4. At this time, information indicating that the sample S has been placed at the distant position Pr is displayed on a display device (not shown) provided in a predetermined position of the thermal analysis apparatus 1. When the operator who has confirmed the information wants to perform take-out or replacement of the sample S, he or she slides the knob 61 in the direction of the arrow C to open the shutter 60. Through the shutter 60 thus opened, the sample S is taken out or replaced by another sample S.

As shown in FIG. 1A, the pull out table (that is, a drawable table) 67 is provided at a lower portion of the operating section cover 4. The pull out table 67 can be pulled outside, as shown in FIG. 1B. In FIG. 8B, operators can drop the sample S or the reference substance R by mistake when he or she takes them outside or puts them inside through the opening 59 with the shutter 60 being opened. Since the dropped sample S or the like is received by the pull out table 67 contained in the operating section cover 4, operators easily get back the dropped sample S by pulling the pull out table 67 outside as shown in FIG. 1B.

As described above, according to the thermal analysis apparatus 1 of the present embodiment, when the sample S shown in FIG. 4 needs to be taken out of the sample temperature control unit 8, the sample temperature control unit 8 is not moved, but the housing 18 is allowed to slide. The slide of the housing 18 brings the sample-side balance beam 23b sliding to thereby convey the sample S to the distant position Pr which is a position outside the sample temperature control unit 8. Therefore, even when the heavy sample temperature control unit 8 is employed or accessories such as a gas supplying tube are provided in the sample temperature control unit 8, a structure for performing replacement of the sample S, such as the sample moving unit 7 shown in FIG. 3, can be configured in a small size and in a simple manner.

It is preferable that the movement speed of the balance beams 23a and 23b be gradually increased to a predetermined speed when they start to linearly slide in the direction of the arrow A from the first position shown in FIG. 4, or when they start to rotationally slide in the direction of the arrow B' from the second position shown in FIG. 8A. That is, it is preferable to perform a so-called slow start. Further, it is preferable that the movement speed of the balance beams 23a and 23b be gradually decreased when they are stopped at the first position (FIG. 4) or the second position (FIG. 8A). That is, it is preferable to perform a so-called slow stop. Such a speed control prevents the balance beam from being damaged or deformed and prevents the sample or the like from being dropped from the balance beam. The speed control described above can be achieved by, for example, control of the rotation speed for the output shaft of the motor.

It is preferable that the movement speed of the balance beams 23a and 23b be gradually increased to a predetermined speed when they start to rotationally slide in the direction of the arrow B in FIG. 8A after finishing to linearly slide in the direction of the arrow A in FIG. 7. In addition, it is preferable that the movement speed of the balance beams 23a and 23b be gradually increased to a predetermined speed when they start to linearly slide in the direction of the arrow A' after finishing to rotationally slide in the direction of the arrow B'. Such a speed control prevents the balance beam from being damaged or deformed and prevents the sample or the like from being dropped from the balance beam. The speed control described above can be achieved by, for example, control of the rotation speed of the motor. Alternatively, by making a partial change in the tooth shapes of the gear member 56 and the rack 57, the above speed control can be obtained.

As shown in FIG. 1A, all the mechanisms for carrying out thermal analysis measurement are disposed within a space surrounded by the cover 2, the covers 3a to 3c, and the operating section cover 4, so that the balance beam and the like are not exposed to air atmosphere, allowing a correct weight measurement. Further, as shown in FIG. 8A, the opening 59 is provided in the operating section cover 4 at the portion corresponding to the distant position Pr of the sample S, making it easy to take out and put in the sample S and the like through the opening 59.

As shown in FIG. 8A, the distant position Pr of the sample S is defined as the position at which the sample S is deviated from the line trajectory L0 in the lateral direction (that is, the downward direction of FIG. 8A). With this configuration, even if the sample S is dropped from the balance beam 23b, it is possible to prevent the main mechanism of the thermal analysis apparatus 1 from being hit and damaged by the dropped sample S. Further, it is possible to move the sample S near the operator, making it easy for the operator to perform replacement of the sample S.

In FIG. 5A, the second beams 25a and 25b constituting the balance beams 23a and 23b are detachably attached to the first beams 24a and 24b. Detaching the second beams 25a and 25b from the first beams 24a and 24b is achieved by removing the plug portions 27a and 27b of the second beams 25a and 25b from the socket portions 26a and 26b of the first beams 24a and 24b. On the other hand, Attaching the second beams 25a and 25b to the first beams 24a and 24b is achieved by fitting the plug portions 27a and 27b of the second beams 25a and 25b to the socket portions 26a and 26b of the first beams 24a and 24b. Since the housing 18 is made of an opaque metal material or an opaque resin material in a conventional thermal analysis apparatus, it is necessary to remove the upper cover of the housing 18 for visual confirmation of the inside of the housing 18 in order to accomplish the attachment and detachment between the plug portion and socket portion. Removing and re-fitting of the upper cover is very troublesome. On the other hand, in the present embodiment, the upper cover 17 of the housing 18 is made of a transparent material, so that the operator can visually confirm the connection portions of the balance beams 23a and 23b through the upper cover 17. Therefore, it is possible to accomplish the attachment and detachment between the first beams 24a, 24b and the second beams 25a, 25b without removal of the upper cover 17, making it easier to attach and detach the second beams 25a and 25b.

Another Embodiment

In FIG. 8A, the distant position Pr of the sample S is defined as the position that is deviated laterally from the line trajectory L0. Alternatively, however, it is possible to set an appropriate position on the line trajectory L0 as the distant position Pr of the sample S. Also in this case, it is possible to perform replacement of a sample not by moving the sample temperature control unit 8 but by moving the balance beam 23b, thereby achieving the object of the present invention.

In FIG. 5A, the balance mechanism 21a for the reference substance R is employed in addition to the balance mechanism 21b for the sample S. However, the present invention can also be applied to a TG apparatus having a configuration in which only the balance mechanism 21b for the sample S is employed.

Although the present invention is applied to a TG-DTA apparatus in the embodiment described above, the present invention can also be applied to another type of thermal analysis apparatus, such as a TG apparatus, a DTA apparatus, and a DSC apparatus. In the case where the present invention is applied to the TG apparatus, a DTA function is unnecessary, eliminating the need to provide the DTA measurement circuit 31 in FIG. 5 and the need to fix the thermocouple wire to the thermosensitive plates 30a and 30b. In the case where the present invention is applied to the DTA apparatus, the balance mechanism is unnecessary, so that a configuration that uses a long supporting bar in place of the balance beam to support a sample can be adopted. In the case where the present invention is applied to the DSC apparatus, a configuration that uses a long supporting bar to support a sample stage provided with a thermosensitive plate for DSC can be adopted.

Figure 9:
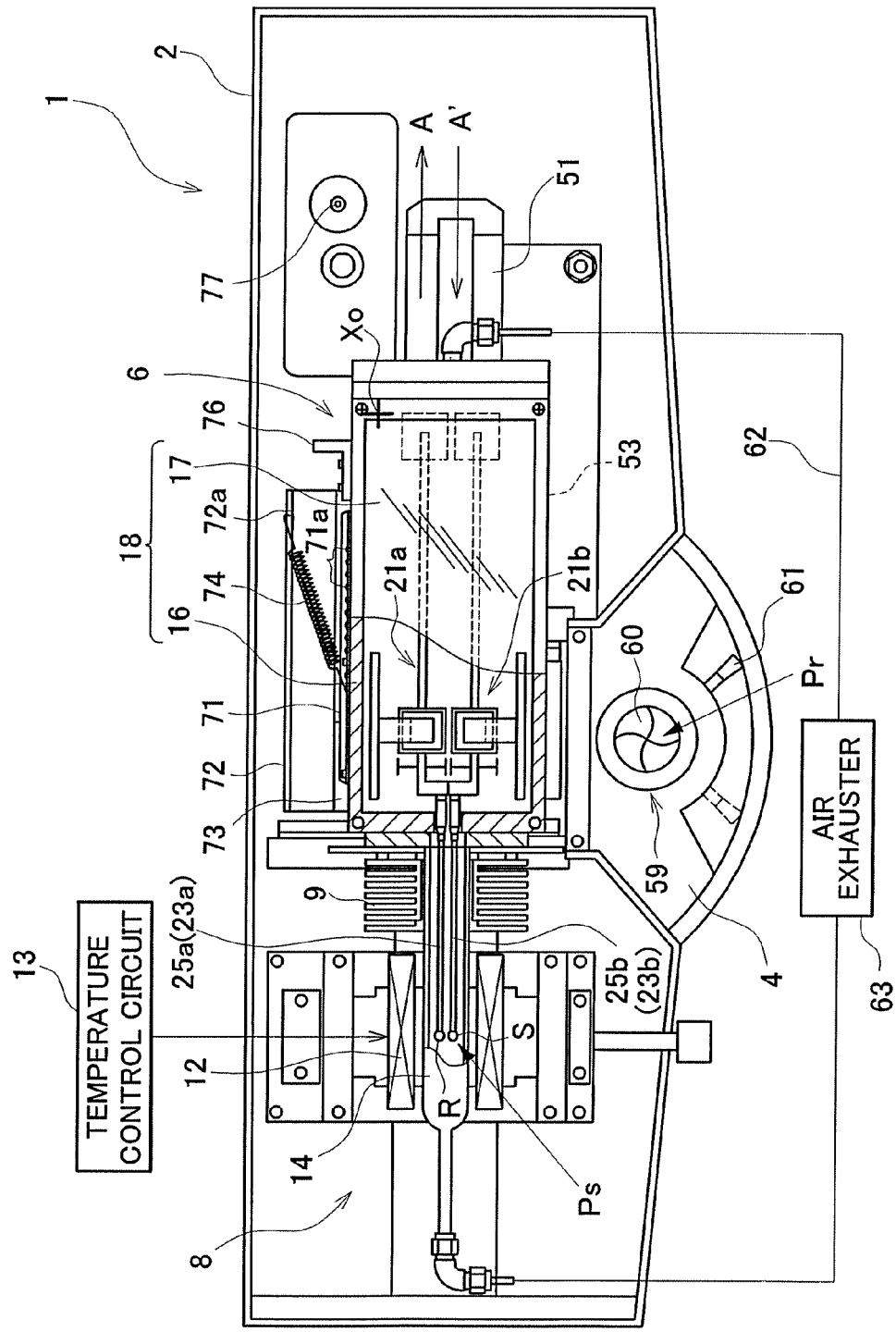
FIG. 9 is a cross-sectional plan view of another embodiment of the thermal analysis apparatus according to the present invention.
Figure 10:
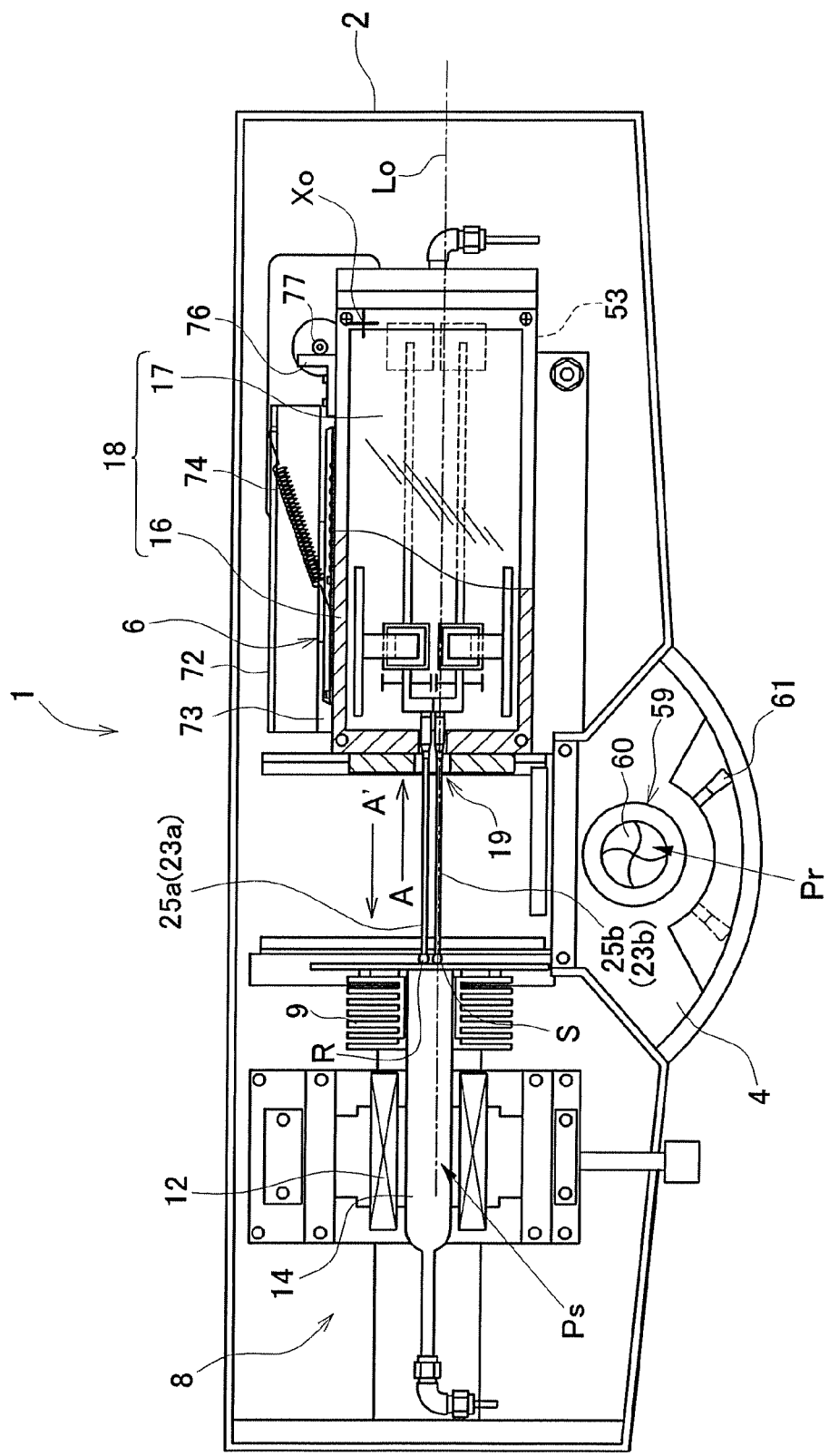
FIG. 10 is a view showing a state of movement of the structure shown in FIG. 9.
Figure 11:
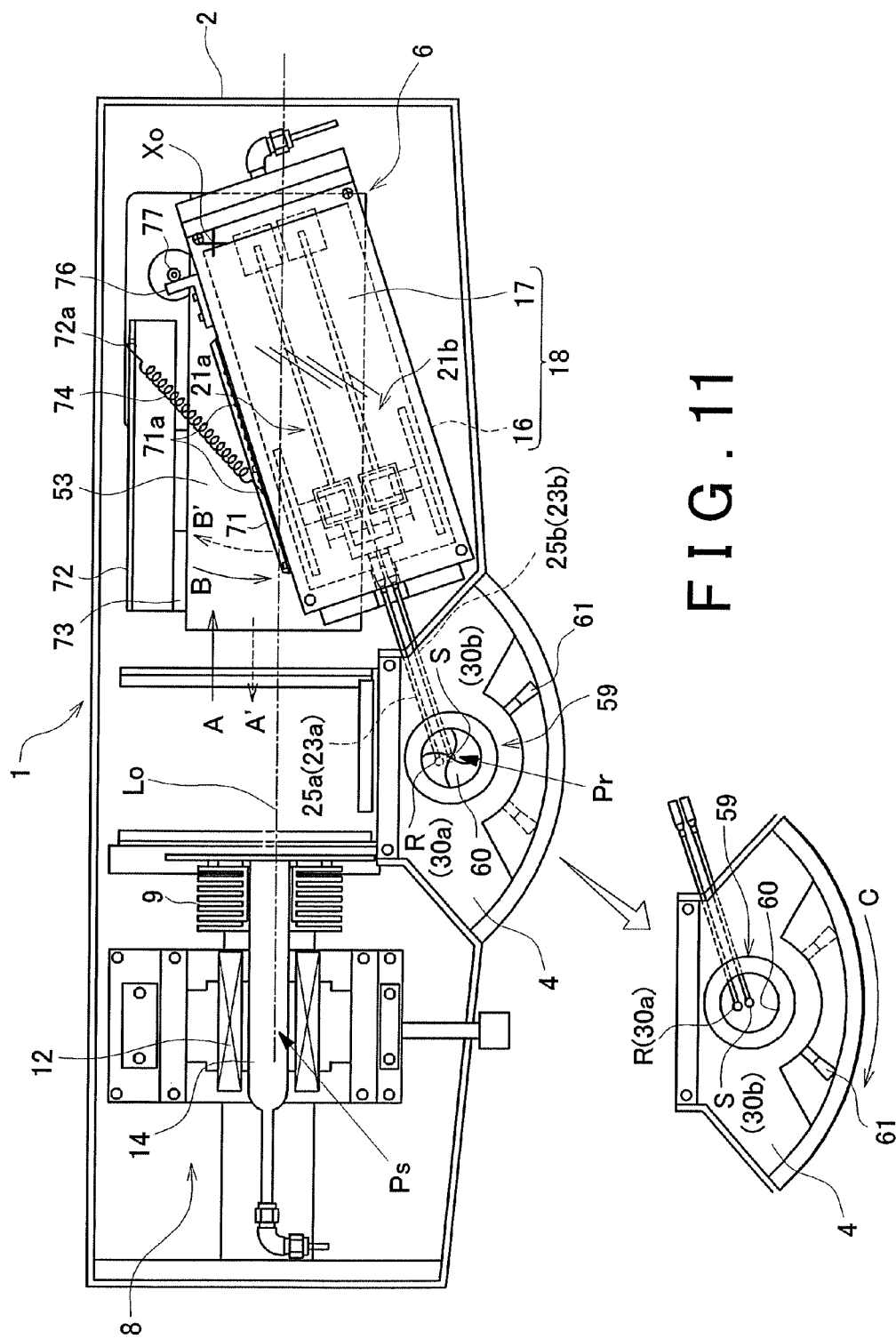
FIG. 11 is a view showing another state of movement of the structure shown in FIG. 9.

The thermal analysis apparatus shown in FIG. 4 includes the mechanism for rotationally moving the housing 18 about the axial line X0, and the mechanism includes the gear member 56 and the rack 57. Alternatively, however, another mechanism may be adopted in the present invention, for example, as shown in FIGS. 9 to 11. This mechanism includes an L-shaped contact member 76, a pole member 77 and a coil spring 74. The pole member 77 is immovably provided at the right corner inside the cover 2 and extends in a direction perpendicular to the plane of FIG. 9.

A first bracket 71 having a plate shape is fixed to one side of the box-formed base body 16. The first bracket 71 has a plurality of hook portions 71a at the upper portion thereof. As shown in FIG. 11, the unit base plate 53 is equipped with a stopper 73 and a second bracket 72. The second bracket 72 has a hook portion 72a at the upper portion thereof. One end of the coil spring 74 is hooked to any desired one of the plurality of hook portions 71a of the first bracket 71. The other end of the coil spring 74 is hooked to the hook portion 72a of the second bracket 72. In FIG. 9 the base body 16 is urged by the coil spring 74 to rotate clockwise about the axial line X0, and is brought into contact with the stopper 73.

In FIG. 9 the housing 18 places the sample S at the measurement position Ps. If the unit base plate 53 is driven to slide linearly by a predetermined distance in the direction shown by the arrow A, the contact member 76 hit the pole member 77 as shown in FIG. 10. Further sliding of the unit base plate 53 in the direction shown by the arrow A causes a rotation moment around the axial line X0 to the housing 18 at a contact point between the contact member 76 and the pole member 77. Due to the rotation moment, the housing 18 slide rotationally counterclockwise about the axial line X0 against biasing force of the coil spring 74 as shown in FIG. 11, to thereby convey the sample S from a position on the line trajectory L0 to the distant position Pr.

Later, the unit base plate 53 is driven to slide linearly in the direction shown by the arrow A'. Then, the housing 18 rotates clockwise about the axial line X0, so that the sample S supported by the housing 18 through the second beam 25b of the balance beam 23b is conveyed back from the distant position Pr to the position on the line trajectory L0 as shown in FIG. 10. Further sliding of the unit base plate 53 in the direction shown by the arrow A' places the sample S at the measurement position Ps as shown in FIG. 9. Thus, the sample S is enabled to be measured for a thermal analysis.

In this embodiment of the present invention the mechanism for rotationally moving the housing 18 about the axial line X0 includes the contact member 76, the pole member 77 and the coil spring 74. This mechanism may be simple in structure and stable in operation without malfunction.

What is claimed is:

1. A thermal analysis apparatus comprising:
   a sample temperature control unit for surrounding a sample placed on a measurement position and controlling the temperature of the sample;
   a balance beam for supporting the sample and capable of tilting about a pivot point;
   a sample moving unit for allowing the balance beam to slide between a first position at which the sample is situated at the measurement position and a second position at which the sample is situated at a distant position which is a position outside the sample temperature control unit.

2. The thermal analysis apparatus according to claim 1, wherein the distant position of the sample is a position which is deviated laterally from a line trajectory extending from the measurement position to the outside of the sample temperature control unit.

3. The thermal analysis apparatus according to claim 2, comprising a cover surrounding the sample temperature control unit and the balance beam, the cover having, at a portion corresponding to the distant position of the sample, an opening through which the sample is taken out and put in.

4. The thermal analysis apparatus according to claim 3, wherein the sample moving unit has
   a liner movement unit for allowing the balance beam to linearly slide and
   a rotational movement unit for allowing the balance beam to rotationally slide, and
   the distant position of the sample is a position which is deviated laterally from a linear sliding path on which the sample is moved by the linear movement unit.

5. The thermal analysis apparatus according to claim 4, wherein the rotational movement unit has:
   a gear member integrated with the balance beam so as not to be rotatable relative to the balance beam; and a rack immovably provided in a position at which it can engage with the gear member.

6. The thermal analysis apparatus according to claim 5, wherein
the moving speed of the balance beam is gradually increased when it starts to slide rotationally after completion of its linearly sliding and/or when it starts to slide linearly after completion of its rotationally sliding.

7. The thermal analysis apparatus according to claim 6, wherein
the sample moving unit gradually increases the moving speed of the balance beam when the balance beam starts its sliding from the first position or second position and/or gradually decreases the moving speed of the balance beam when the balance beam stops its sliding toward the first position or second position.

8. The thermal analysis apparatus according to claim 1, comprising a cover surrounding the sample temperature control unit and the balance beam, the cover having, at a portion corresponding to the distant position of the sample, an opening through which the sample is taken out and put in.

9. The thermal analysis apparatus according to claim 1, wherein the sample moving unit has
a liner movement unit for allowing the balance beam to linearly slide and
a rotational movement unit for allowing the balance beam to rotationally slide, and
the distant position of the sample is a position which is deviated laterally from a linear sliding path on which the sample is moved by the linear movement unit.

10. The thermal analysis apparatus according to claim 1, wherein
the sample moving unit gradually increases the moving speed of the balance beam when the balance beam starts its sliding from the first position or second position and/or gradually decreases the moving speed of the balance beam when the balance beam stops its sliding toward the first position or second position.

11. The thermal analysis apparatus according to claim 2, wherein the sample moving unit has
a liner movement unit for allowing the balance beam to linearly slide and
a rotational movement unit for allowing the balance beam to rotationally slide, and
the distant position of the sample is a position which is deviated laterally from a linear sliding path on which the sample is moved by the linear movement unit.

12. The thermal analysis apparatus according to claim 2, wherein
the sample moving unit gradually increases the moving speed of the balance beam when the balance beam starts its sliding from the first position or second position and/or gradually decreases the moving speed of the balance beam when the balance beam stops its sliding toward the first position or second position.

13. The thermal analysis apparatus according to claim 3, wherein
the sample moving unit gradually increases the moving speed of the balance beam when the balance beam starts its sliding from the first position or second position and/or gradually decreases the moving speed of the balance beam when the balance beam stops its sliding toward the first position or second position.

14. The thermal analysis apparatus according to claim 4, wherein
the moving speed of the balance beam is gradually increased when it starts to slide rotationally after completion of its linearly sliding and/or when it starts to slide linearly after completion of its rotationally sliding.

15. The thermal analysis apparatus according to claim 4, wherein
the sample moving unit gradually increases the moving speed of the balance beam when the balance beam starts its sliding from the first position or second position and/or gradually decreases the moving speed of the balance beam when the balance beam stops its sliding toward the first position or second position.

* * * * *